United States Patent
Hoang et al.

(10) Patent No.: US 6,531,161 B1
(45) Date of Patent: Mar. 11, 2003

(54) METHOD FOR TREATMENT OF CHRONIC IDIOPATHIC THROMBOCYTOPENIC PURPURA (ITP)

(75) Inventors: Ba X. Hoang, San Jose, CA (US); Stephen A. Levine, San Raphael, CA (US)

(73) Assignee: Allergy Research Group/Nutricology, Inc., Hayward, CA (US)

( * ) Notice: Subject to any disclaimer, the term of this patent is extended or adjusted under 35 U.S.C. 154(b) by 0 days.

(21) Appl. No.: 09/788,203

(22) Filed: Feb. 15, 2001

Related U.S. Application Data

(63) Continuation of application No. 09/771,253, filed on Jan. 26, 2001.
(60) Provisional application No. 60/178,120, filed on Jan. 26, 2000.

(51) Int. Cl.[7] .................................................. A61K 38/78
(52) U.S. Cl. ....................... 424/725; 424/773
(58) Field of Search .............................. 424/78.36, 725, 424/78.3, 439, 441, 773; 514/866, 909

(56) References Cited

U.S. PATENT DOCUMENTS 6,093,403 A * 7/2000 Huo et al. ................. 424/725

* cited by examiner

Primary Examiner—Christopher R. Tate
Assistant Examiner—Kailash C. Srivastava
(74) Attorney, Agent, or Firm—Peter J. Dehlinger; Perkins Coie LLP

(57) ABSTRACT

The invention provides for compositions and methods for treating a patient suffering from chronic idiopathic thrombocytopenic purpura, and methods for making the composition. In preferred embodiments, the composition is made from several plant or herbs including: Radix Astragalus, Rehmania glutinosa, Rhizoma Acori gramenei, Rhizoma Alismatis, and Rhizoma Smilacis glabrae. The composition may be made in the form of an aqueous extract or decoction of the several or combined plants or herbs, or may be formed as a dry composition to be administered as a pill or suspension. The invention provides for an effective, low cost, simple to administer treatment for chronic idiopathic thrombocytopenic purpura, especially in otherwise refractive cases.

4 Claims, No Drawings

METHOD FOR TREATMENT OF CHRONIC IDIOPATHIC THROMBOCYTOPENIC PURPURA (ITP)

PRIORITY

This patent application claims priority to U.S. application Ser. No. 09/771,253 filed Jan. 26, 2001, which claims priority under 35 U.S.C. §119(e) to provisional patent application No. 60/178,120, filed Jan. 26, 2000 which is herein incorporated by reference in its entirety.

FIELD OF THE INVENTION

This invention relates to the field of medicine, pharmaceuticals, herbal remedies, and specifically to the treatment of chronic idiopathic thrombocytopenic purpura, especially in cases where the patient is refractive to other treatments.

BACKGROUND OF THE INVENTION

Idiopathic thrombocytopenic purpura (ITP), also known as primary immune thrombocytopenic purpura and autoimmune thrombocytopenic purpura, is defined as isolated thrombocytopenia with normal bone marrow and the absence of other causes for thrombocytopenia. "Idiopathic" indicates that the cause is unknown, "Thrombocytopenic" indicates the blood doesn't have enough platelets, and "Purpura" indicates a person has excessive bruising. For the two types of ITP, the first type affects children, and the second type affects adults. In children, the usual age of onset for ITP is about two to four years of age. Most adults with ITP are young women, but ITP can occur in anyone.

ITP affects women more frequently than men and is more common in children than adults. There is no sex difference in children. Risk factors are unknown. The incidence is 1 out of 10,000 people.

In the US: The incidence of ITP in adults is approximately 66 cases per 1,000,000 per year. An average estimate of the incidence in children is 50 cases per 1,000,000 per year. New cases of chronic refractory ITP are approximately 10 cases per 1,000,000 per year. Internationally: According to studies in Denmark and England, childhood ITP occurs in approximately 10–40 cases per 1,000,000 per year. A study in Kuwait reported a higher incidence of 125 cases per 1,000,000 per year.

This problem is significant because chronic ITP is one of the major blood disorders in both adults and children. They are a source of significant hospitalization and treatment cost at specialized hematological departments in the US and around the world. Approximately 100,000 people in the US have ITP. The percentage rate of ITP cases is increasing. Each year there are approximately 20,000 new cases in the US. More importantly the cost for ITP care and special therapy is extremely high.

ITP is different in children than in adults. Most children with ITP have a very low platelet count that causes sudden bleeding. The usual symptoms are bruises and the tiny red dots on the skin. Nosebleeds and bleeding gums are also common. Although children often recover with no treatment, many doctors recommend careful observation and mitigation of the bleeding symptoms. Children do not always require hospitalization, and often a short treatment with prednisone pills or intravenous infusions (given in a vein) of gamma globulin to increase the platelet count more quickly. Both treatments, however, have substantial side effects and it is therefore desirable to identify a safe and effective remedy for ITP in children which does not have the side effects of the prednisone pills or gamma globulin.

Typically, in most adults, ITP lasts much longer than it does in children. When diagnosed, many adults present increased bleeding and tend to bruise easily for several weeks, or even months. In women, increased menstrual blood flow is a good indicator of ITP.

In cases of adult mild thrombocytopenia, there are often no bleeding symptoms and the diagnosis of ITP occurs when their blood is checked for another reason and a low blood platelet count is found.

Traditional treatment of ITP in adults is aimed at increasing the blood platelet count by suppressing the immune system which then permits accumulation of platelets without changing the nature of the platelets. This does not the cure the patient of the disease. Patients may take prednisone for several weeks, even a month or longer. However, when the medicine is stopped, platelet counts may return to below normal levels.

With patients refractive to prednisone, a spleenectomy may be indicated. In chronic ITP patients, it is the spleen that makes most of the antibodies that destroy the blood platelets and destroys old or damaged blood cells. Removal of the spleen is a dramatic and permanent alteration of the patient's body, and includes all the associated potential complications associated with major surgical procedures such as reactions to anesthesia and infection.

In people with ITP, blood cells are normal except for the blood platelets. Platelets are the tiny cells that seal minor cuts and wounds and form blood clots. A person with too few platelets bruises easily and bleeds for a long time after being injured. Tiny red dots on the skin, called petechiae might also appear. When the platelet count is very low, the person with ITP might have nosebleeds that are hard to stop, or might have bleeding in the intestines.

ITP primarily is a disease of increased peripheral platelet destruction, with most patients having antibodies to specific platelet membrane glycoproteins. Relative marrow failure may contribute to this condition, since studies show that most patients have either normal or diminished platelet production. Traditional medical theory purports that platelets and platelet counts would be normal but for the presence of autoimmune antibodies (autoantibodies) made by the patient's body. Accordingly, traditional medicine attempts to treat a chronic ITP patient by suppressing the immune system, and consequently causing an increase in platelet levels.

Since ITP results from a shortage of platelets, a characteristic bleeding under the skin is often associated with the disease. The disease is believed to be caused when the spleen and lymph tissue produce antibodies against platelets. The antibodies destroy the platelets in the spleen. Symptoms include skin hemorrhage, nosebleed or oral bleeding, easy bruising, abnormal menstrual bleeding, or sudden and severe loss of blood from the gastrointestinal tract may occur, and petechial rash (pinpoint red spots).

Usually, no other abnormal findings are present. In children, the disease is sometimes preceded by a viral infection and runs its course without treatment. In adults, it is usually chronic disease and rarely follows a viral infection.

Acute ITP often follows an acute infection and has a spontaneous resolution within two months. Chronic ITP persists longer than six months without a specific cause.

Hemorrhage represents the most serious complication; intracranial hemorrhage is the most significant. Mortality from hemorrhage is approximately 1% in children and 5% in adults. Older age and previous history of hemorrhage increase the risk of severe bleeding in adult ITP. Spontaneous remission occurs in children in greater than 80% of cases, but it is uncommon in adults.

Diagnosis of chronic ITP often includes examining the patient for an enlarged spleen. Additional tests include CBC with platelet count, bone marrow aspiration or biopsy, PTT (coagulation studies), PT (coagulation studies), platelet associated antibodies, platelet aggregation test Typical treatment of ITP involves initial treatment with prednisone. A splenectomy (removal of the spleen) is indicated if the person does not respond to prednisone. The spleen is the major site of platelet destruction, so a splenectomy will resolve the thrombocytopenia in most people.

Other treatments (when the disease does not respond to initial treatment) are oral danazol, high dose gamma globulin injections, drugs that suppress the immune system, and passage of the blood over a Protein A (Prosorba) column (which filters antibodies out of the blood stream). People with ITP should avoid taking aspirin or ibuprofen, because bleeding may occur.

With acute ITP, the chance of remission is good with prednisone or splenectomy, however, ITP may often become a chronic ailment in adults and reappear even after remission.

The treatment for chronic ITP is indicated generally in patients who are unable to maintain platelet counts consistently over 30,000/µl. Initial specific treatment is corticosteroids and Splenectomy (surgical removal of the spleen) if the first therapy failed. The treatment of patients who fail to respond to corticosteroids and splenectomy is often difficult since these patients tend to be resistant to many forms of treatment. More significantly all types of therapy are either of questionable value, of limited value or require further study. Also, the treatment of all levels is associated with progressively serious early or late side effects. The cost of each therapy is often very high and the administering methods are also complicated. The following is a description of three levels of treatment:

In traditional medicine, first line treatments include using; corticosteroids, splenectomia, vinca alkaloids (vincristine or vinblastine), Danazol (Danocrine), Colchicine, and Dasone. Second line treatments include using; Staph Protein A Column (Prosorba Colum), Cyclophosphamide (cytoxan), and Azathioprine (Immuran). Third line treatments include using; combination chemotherapy, and high-dosage cyclophosphamide. Treatment of questionable or limited benefit include using; Anti-D Antibody, High dosage of Ascorbic Acid (vitamin C), Cyclosporine, Intravenous Immunoglobuline G -IVIG, and Interferon.

All of the above treatments either do not, or rarely cure a patient of chronic ITP. Moreover, each of the compounds and treatments described above have serious side effects, are costly, and generally do not cure the patient. Accordingly, a treatment for chronic idiopathic thrombocytopenic purpura (ITP) or chronic autoimmune thrombocytopenia which is simple to use, has no or little side effects, is needed. Such treatment would include therapeutic compounds which cause quick resolution of the symptoms of chronic ITP, which improves platelet counts and normalizes such for the majority of the treated chronic ITP patients, results in remission and recovery of a high percentage of such patients, which is effective for patients who did not respond to other therapy, which improves the patient's quality of life and social adaptation, which is effective in patients with refractory ITP, and which causes minimal, if any, adverse side effects.

The invention described herein meets these and other important needs.

SUMMARY OF THE INVENTION

In comparison to traditional therapy (whose goal is to destroy or suppress immune system) our unique therapeutic composition not only modulates immunopathological reaction, but also promotes the elimination of the underlying causes of chronic ITP as listed above.

The invention provides, in one aspect, for a composition formed from a decoction or powder of the following ingredients: Radix Astragali and Radix or fresh root of Rehmanniae, in addition to one or more herbs selected from the group consisting of Rhizoma Cyperi, Rhizoma Acori gramenei, Rhizoma Alismatis or Rhizoma Alisma, and Rhizoma Smilacis glabrae. The composition is an effective and safe medicine to treat all forms of chronic ITP in adults and children.

In another aspect, the invention provides for methods and compositions for treating a patient suffering from chronic idiopathic thrombocytopenic purpura, or threatened with chronization of the same, and methods for making the same. In one aspect, the invention provides for an aqueous decoction of a combination of the herbs Radix Astragalus and fresh root of Radix Rehmania glutinosa, and further includes one or more herbs selected from the group consisting of Rhizoma Acori gramenei, Rhizoma Cyperi, Rhizoma Alismatis, and Rhizoma Smilacis glabrae.

In another aspect, the invention provides for a kit for making an aqueous decoction of a composition for treating a patient suffering from chronic idiopathic thrombocytopenic purpura, or threatened with chronization of the same. In some of the preferred embodiments, the kit contains a combination of the herbs Radix Astragalus and Rehmania glutinosa, and further including one or more herbs selected from the group consisting of Rhizoma Acori gramenei, Rhizoma Cyperi, Rhizoma Alismatis, and Rhizoma Smilacis glabrae, in a form adapted for aqueous decocting, and, optionally, instructions for making said aqueous decoction from about equal weight portions of said herbs.

In another aspect, the invention provides for a method for treating a patient suffering from chronic idiopathic thrombocytopenic purpura, or threatened with chronization of the same. In preferred embodiments, the method includes the steps of;

(a) diagnosing said patient as having chronic idiopathic thrombocytopenic purpura by at least measuring blood platelet counts and determining such counts to be below normal, (b) providing to said patient a decoction of a combination of the herbs Radix Astragalus and fresh root or Radix Rehmania glutinosa, and further including one or more herbs selected from the group consisting of Rhizoma Acori gramenei, Rhizoma Cyperi, Rhizoma Alismatis, and Rhizoma Smilacis glabrae., (c) administering said decoction to said patient for a selected period of time, (d) monitoring said patient blood levels for platelet count, and (e) discontinuing said administering step upon achieving normal blood platelet counts.

In another aspect, the invention provides for a composition for treating a patient suffering from chronic idiopathic thrombocytopenic purpura, or threatened with chronization of the same. In preferred embodiments, the composition is produced from a method comprising the steps of:

making a combined weight/weight (w/w) ratio of the following weight amounts of herbs including;
    (a) providing between about 10 to 50% w/w Rhemania glutinosa herb,
    (b) providing between about 5–45% w/w Radix Astragalus herb,
    (c) providing between about 0–50% w/w Rhizoma Acori gramenei herb,
    (d) providing between about 0–50% Rhizoma Cyperi herb,
    (e) providing between about 0–50% w/w Rhizoma Alismatis herb, and
    (f) providing between about 0–50% w/w Rhizoma Smilacis glabrae herb,
    such that the combined w/w ratio equals 100%, and
  decocting or combining dry said weight amounts of said herbs either individually or in combination or both to form said composition.

In another aspect, the invention provides for a composition for treating a patient suffering from chronic idiopathic thrombocytopenic purpura, or threatened with chronization of the same. In preferred embodiments, the composition includes;

an aqueous decoction or dry formula of a combined weight/weight (w/w) ratio of the following weight amounts of herbs including;
    (a) between about 10 to 50% w/w Rhemania glutinosa herb,
    (b) between about 5–45% w/w Radix Astragalus herb,
    (c) between about 0–50% w/w Rhizoma Acori gramenei herb,
    (d) between about 0–50% w/w Rhizoma Alismatis herb,
    (e) providing between about 0–50% Rhizoma Cyperi herb, and
    (f) between about 0–50% w/w Rhizoma Smilacis glabrae herb,
    such that said combined w/w ratio equals 100%.

In another aspect, the invention provides for a method for treating a patient suffering from chronic idiopathic thrombocytopenic purpura, or threatened with chronization of the same. In preferred embodiments, the method includes the steps of;

(a) diagnosing said patient with having idiopathic thrombocytopenic purpura,
  (b) providing (an) aqueous decoction(s) or dry formula of a combined weight/weight (w/w) ratio of the following weight amounts of herbs including;
    (i) between about 10 to 50% w/w Rhemania glutinosa herb,
    (ii) between about 0–45% w/w Radix Astragalus herb,
    (iii) between about 0–50% w/w Rhizoma Acori gramenei herb,
    (iv) between about 0–50% w/w Rhizoma Alismatis herb,
    (v) between about 0–50% Rhizoma Cyperi herb, and
    (vi) between about 0–50% w/w Rhizoma Smilacis glabrae herb,
    such that said combined w/w ratio equals 100%,
  (c) administering therapeutic doses of said decoction(s) or dry formula to said patient at selected administration intervals,
  (d) monitoring said patient's blood platelet levels at selected monitoring intervals during said administering step,
  (e) ending said administering when said patient's blood platelet levels become normal.

In another aspect, the invention provides for a method for treating a patient suffering from chronic idiopathic thrombocytopenic purpura, the method comprising the steps of;

(i) stimulating the patient's immune system by administering to the patient an immunological stimulation or activation agent(s), and stimulating the patient's stem cell system with a platelet stimulating agent to produce increased amounts of platelets,
  (ii) maintaining the patient on the immunological stimulating agent and platelet stimulating agent for a selected period of time having and end period, and
  (iii) discontinuing the maintaining until the end period of the selected period of time.

The method above may further include having the immunological stimulating agent and the platelet stimulating agent be supplied in the form of one of the compositions listed above.

The invention provides in a preferred embodiment of one aspect, composition comprising a first component of about 5 to 75% w/w, preferably about 10 to 60% w/w, more preferably about 10–45% w/w, still more preferably about 10 to 30% w/w, yet still more preferably about 10–20% w/w, and particularly preferred at about 20% w/w of Rhemania glutinosa (preferably fresh root). A second component of about 0 to 75% w/w, preferably about 0 to 45% w/w, more preferably about 5 to 30% w/w, still more preferably about 5 to 20%, yet still more preferably about 10 to 20%, and particularly preferred at about 20% w/w of Radix Astragalus. A third component of about 0 to 65% w/w, preferably 0–50% w/w, more preferably about 0 to 30% w/w, still more preferably about 0 to 25%, yet still more preferably about 10 to 25% w/w, and particularly preferred at about 20% w/w of Rhizoma Acori Grameni. A fourth component of about 0 to 65% w/w, preferably 0–50% w/w, more preferably about 0 to 30% w/w, still more preferably about 0 to 25%, yet still more preferably about 10 to 25% w/w, and particularly preferred at about 20% w/w of Rhizoma Alismatis. A fifth component of about 0 to 65% w/w, preferably 0–50% w/w, more preferably about 0 to 30% w/w, still more preferably about 0 to 25%, yet still more preferably about 10 to 25% w/w, and particularly preferred at about 20% w/w of Rhizoma Cyperi. A sixth component of about 0 to 65% w/w, preferably 0–50% w/w, more preferably about 0 to 30% w/w, still more preferably about 0 to 25%, yet still more preferably about 10 to 25% w/w, and particularly preferred at about 20% w/w of Rhizoma Smilacis Glabrae. Each component above is then combined such that the combined w/w ratio of each component equals 100%. Each component of the mixture may be combined and formed into powders for making suspensions, processed into pill form, or decocted or extracted to form, eventually, a concoction of decoctions or extracts.

DETAILED DESCRIPTION OF THE PREFERRED EMBODIMENTS

The invention provides simple, inexpensive, and safe methods and compositions for treating patients suffering from chronic idiopathic thrombocytopenic purpura, and other platelet deficiency related diseases.

Not wishing to be bound in anyway by theory, the invention employs a strategy contrary to both western medicine, and Chinese herbal medicine, to treat an ITP patient. In particular, unlike other methods which increase platelet levels by depressing the immune system to minimize autoantibodies against platelets, the invention enhances the immune system and boosts platelet production directly. Although it might appear that the whatever increases in platelet production achieved would be negatived by the enhancement of the immune system, a surprising result was discovered—platelet production actually increased and remained post therapy. It is thought that by boosting both the platelet production, and the immune system resulted in correction of defective platelet production, such defective platelets being the target of the body's immune system, and therefore the subject of an autoimmune response resulting in the ITP.

Although the preferred embodiment of the invention is described below, it is believed that any immuno stimulating compound(s), and any platelet stimulating compound(s), may be employed in conjunction to achieve the effect of the invention. It is the strategy of the combined stimulation that is believed to result in permanent resolution of the ITP condition within the patient.

Preferred embodiments of the invention employ raw dried herb products, unless noted otherwise. The herb products are typically cooked to make decoctions, or may be combined to form pills, capsules or suspensions. Disclosed are recommended cooking procedures, however, one skilled in the art will realize that many preparation variations are possible. Although it is recognized that each herb has its peculiar requirements depending upon its hardness, ability to absorb water, size and thickness of pieces, and other factors the standard of cooking used in making the compounds of invention assumes, preferably, that most herbs will be soaked in warm water before cooking to allow the cooking water to penetrate gradually;

Treatment of Non-Splenectomized ITP Patients

Fourteen patients with platelet counts at least lower than 30,000/µl are undergoing treatment. Of the fourteen patients, five have history of ITP for more than one year and nine have chronic ITP for more than three years. All patients were non-responders to specific standard therapies for ITP and were recommended to splenectomy (surgical removal of the spleen). All patients are being treated with the invented composition (herbal powder in capsules or a concoction). All patients tolerated well and completed the six-month treatment schedule.

All treated patients achieved a significant improvement of their ITP symptoms in one week of therapy. Symptoms were extensive bruising, nose-bleeding that required hospitalization, and prolonged and profuse mensis.

At twelve weeks, eleven patients had a platelet count higher than 100,000/µ and the remaining three had platelet counts above 50,000/µl. No non-responders have been observed. Six patients achieved normalization of platelets counts (higher than 150,000/µl) after three months of therapy.

Treatment for Refractory ITP

A total of nine patients were enrolled to receive daily treatment with the invented composition. All patients have had platelet counts consistently less than 50,000/µl in more than one year after splenectomia. Among the patients, three were non-responders to any standard therapy and two patients have developed cortocosteroid dependency and three have a short term responses to corticosteroids or IVIG (intravenous immunoglobuline), however the platelet count quickly dropped back to less than 30,000/µl with the cessation of drugs.

All patients were treated with the invented composition for six months. All treated patients experienced a significant reduction in the subjective symptoms of ITP and an improvement with quality of life within 2–8 days. All patients stated a decline in bleeding symptoms including extensive bruising, petechiae, often epitaxis (nose bleeding) and profuse long-lasting menses up to 100% after two weeks of therapy. At three months, four patients have normalized platelet levels (higher than 150,000/µl). The remaining four patients only have slight petechiae with platelet count higher than 50,000/µl. After six months of therapy, seven patients have achieved normalization of platelet counts and the two remaining maintained their significant improvement in quality of life and symptoms of ITP. Their platelet counts were higher than 50,000/µl.

Patients included 10 cases of chronic idiopathic thrombocytopenic purpura (ITP) ages 16 to 54 in a clinical trial lasting about four years. These patients were administered the preferred composition of the invention and followed for between 6 months to 4 years.

The diagnosis criteria included performing a bone marrow smear to determine whether the patient displayed typical megakaryocytic hyperplasia with increasing megakaryocytic numbers. Typically, platelet counts in peripheral blood were less than 20,000/µl for more than one year. All patients displayed severe to moderate hemorrhages: petechiae, ecchymoses and often epistaxis. Three females also suffered long-lasting and sometimes profused menses.

The diagnosis of chronic ITP was established only after the exclusion of secondary ITP such as chronic hepatitis and nephritis, aplastic anemia, hypersplenism, malignant tumor, connective tissue disease and chemical, physical, toxic, and allergenic agents. All of these patients have been treated unsuccessfully with one or a combination of the following drugs: Prednisolone, Umuran, IVIg, and WhinRo. Three of the patients have also been unsuccessfully treated with a splenectomia. The patients activities and quality of life were hampered to substantially impaired due to the disease and complication of traditional therapy.

The therapeutic efficacy of the treatment was evaluated by establishing four therapeutic efficacy categories, each varying in the degree of therapeutic effectiveness as measured by the degree of post-treatment hemorrhaging and platelet count. The categories included:

Absolute effect: hemorrhage stopped, platelet counts returned to higher that 150,000/µl, and no recurrence occurring for at least three months after the therapy discontinued.

Remarkable effect: hemorrhage ceased, platelet counts increased to higher than 100,000/µl.

Good effect: hemorrhage alleviated, platelet counts increased to higher that 50,000/µl.

No effect: no improvement was attained after treatment in platelet counts and the symptom of hemorrhages.

Ten cases treated by herbal pills, including four males and six females, with ages ranging from 16 to 54 years old, and presenting a duration of illness ranging from 13 months to 12 years. Since the individual dosages and courses of treatment were different, platelet counts on admission and discharge were taken for statistical analyses.

The results demonstrated that the mean platelet count of the cases with herbal pills was 22,900/µl before treatment, and 105,500/µl after three months of treatment. Absolute effect was found in four patients, remarkable effect in three patients, and good effect in three patients. All ten patients have been able to reduce and completely be free from drug treatments in three months and have no hospitalizations or bleeding symptoms during the course of herbal therapy.

After six months, absolute effect was found in six patients, remarkable effect in two patients, and good effect in two patients. The mean platelet count of the patients was 128,000/μl. All patients reported a remarkable improvement in the quality of their life, the reduction of their hemorrhagic symptoms, and that they experienced no side effects from the therapy.

Of the three patients that were unresponsive to their splenectomia, each achieved absolute effects with a mean platelet level of 207,000/μl consistently after six months of therapy.

References for providing guidance as to how to make extracts, decoctions, pills and suspensions, each of which is incorporated by reference in their entirety.

Wicke, Roger; *Traditional Chinese Herbal Science: volume 1, The Language and Patterns of Life* (5th edition); Rocky Mountain Herbal Institute, Hot Springs, Mont., c1994.

Wicke, Roger; *Traditional Chinese Herbal Science: volume 2, Herbs, Strategies and Case Studies* (4th edition); Rocky Mountain Herbal Institute, Hot Springs, Mont., c1994.

*Chinese Herbal Medicine: Materia Medica;* Dan Bensky and Andrew Gamble, ed.; Eastland Press, Seattle, c1986.

*A Clinical Guide to Chinese Herbs and Formulae;* by Chen Song Yu and Li Fei, transl. by Jin Hui De; Churchill Livingstone, c1993.

Yeung, Him-che; *Handbook of Chinese Herbal Formulas, vol.* 1 [materia medica] and vol. 2 [formulas]; Los Angeles, c1983.

We claim:

1. A composition for treating a patient suffering from chronic idiopathic thrombocytopenic purpura, or threatened with chronization of the same, consisting essentially of:

an aqueous decoction formed by a decocting method or a dry formula of a combination of the following herbs: Radix Astragalus, Rehmania glutinosa, and one or more herbs selected from the group consisting of Rhizoma Acori gramenei, Rhizoma Alismatis, Rhizoma Cyperi, and Rhizoma Smilacis glabrae.

2. The composition of claim 1, wherein said combination is made from equal weight ratios of Radix Astragalus, Rehmania glutinosa, Rhizoma Acori gramenei, Rhizoma Alismatis, and Rhizoma Smilacis glabrae.

3. The composition of claim 2, wherein said herbs are decocted at a weight to liquid ratio of 10 grams dry weight for each herb in 400 ml of water.

4. The composition of claim 3, wherein said herbs were decocted at 100 degrees centigrade for 30 minutes and then filtered.

* * * * *